(12) United States Patent
Penny et al.

(10) Patent No.: US 11,119,105 B2
(45) Date of Patent: Sep. 14, 2021

(54) FLUID ACTUATION OF INSTRUMENTS THROUGH A STERILE BARRIER

(71) Applicant: Asensus Surgical US, Inc., Durham, NC (US)

(72) Inventors: Matthew R Penny, Holly Springs, NC (US); Kevin Andrew Hufford, Cary, NC (US); Nicholas J Bender, Raleigh, NC (US); Alexander John Maret, Apex, NC (US); Paul Wilhelm Schnur, Pipersville, PA (US); Sevan Abashian, Morrisville, NC (US); Dustin Vaughan, Morrisville, NC (US)

(73) Assignee: Asensus Surgical US, Inc., Durham, NC (US)

( * ) Notice: Subject to any disclaimer, the term of this patent is extended or adjusted under 35 U.S.C. 154(b) by 330 days.

(21) Appl. No.: 15/957,679

(22) Filed: Apr. 19, 2018

(65) Prior Publication Data

US 2018/0238883 A1 Aug. 23, 2018
US 2021/0247396 A9 Aug. 12, 2021

Related U.S. Application Data

(63) Continuation of application No. 15/885,792, filed on Jan. 31, 2018.
(Continued)

(51) Int. Cl.
*G01N 33/573* (2006.01)
*G01N 33/68* (2006.01)
(Continued)

(52) U.S. Cl.
CPC .......... *G01N 33/573* (2013.01); *A61B 17/00* (2013.01); *A61B 34/30* (2016.02); *A61B 34/37* (2016.02);
(Continued)

(58) Field of Classification Search
CPC ............. G01N 33/573; G01N 33/6893; G01N 2333/25; G01N 2800/065; G01N 2800/52; G01N 2333/922; G01N 2333/24; A61B 17/00; A61B 34/74; A61B 46/00; A61B 34/37; A61B 46/10; A61B 34/30; A61B 34/76; A61B 2017/00539; A61B 2017/00477; A61B 2034/302;
(Continued)

(56) References Cited

U.S. PATENT DOCUMENTS 4,488,523 A 12/1984 Shichman
5,339,723 A 8/1994 Huitema
(Continued)

OTHER PUBLICATIONS

PCT, International Search Report and Written Opinion of the International Search Authority for International Application No. PCT/US2018/016324. (dated May 21, 2018).
(Continued)

*Primary Examiner* — Tarla R Patel

(57) ABSTRACT

A robotic surgical system includes a fluid drive system and a surgical instrument removably positioned in operative engagement with the drive system. A sterile barrier covers non-sterile portions of the surgical system. Features of the sterile barrier are used to transfer motion output from the fluid drive system to the instrument for actuation of the instrument.

12 Claims, 7 Drawing Sheets

Related U.S. Application Data

(60) Provisional application No. 62/452,953, filed on Jan. 31, 2017, provisional application No. 62/452,950, filed on Jan. 31, 2017, provisional application No. 62/585,655, filed on Nov. 14, 2017.

(51) Int. Cl.

| | | |
|---|---|---|
| *A61B 46/00* | (2016.01) | |
| *A61B 34/37* | (2016.01) | |
| *A61B 46/10* | (2016.01) | |
| *A61B 34/30* | (2016.01) | |
| *A61B 34/00* | (2016.01) | |
| *B25J 9/14* | (2006.01) | |
| *B25J 18/00* | (2006.01) | |
| *A61B 17/00* | (2006.01) | |

(52) U.S. Cl.
CPC .............. *A61B 34/74* (2016.02); *A61B 34/76* (2016.02); *A61B 46/00* (2016.02); *A61B 46/10* (2016.02); *B25J 9/14* (2013.01); *B25J 18/002* (2013.01); *G01N 33/6893* (2013.01); *A61B 2017/00477* (2013.01); *A61B 2017/00539* (2013.01); *A61B 2034/302* (2016.02); *G01N 2333/24* (2013.01); *G01N 2333/25* (2013.01); *G01N 2333/922* (2013.01); *G01N 2800/065* (2013.01); *G01N 2800/52* (2013.01)

(58) Field of Classification Search
CPC .... A61B 17/00234; A61B 2017/00535; A61B 2017/00318; A61B 2017/003; A61B 2034/301; A61B 46/23; A61B 2046/234; A61B 2046/236; B25J 9/14; B25J 18/002
See application file for complete search history.

(56) References Cited

U.S. PATENT DOCUMENTS

| | | |
|---|---|---|
| 6,755,338 B2 | 6/2004 | Hahnen et al. |
| 6,830,174 B2 | 12/2004 | Hillstead et al. |
| 7,503,474 B2 | 3/2009 | Hillstead et al. |
| 7,922,742 B2 | 4/2011 | Hillstead |
| 8,043,328 B2 | 10/2011 | Hahnen |
| 8,746,533 B2 | 6/2014 | Whitman et al. |
| 9,579,101 B2 | 2/2017 | Whitman et al. |
| 2004/0243176 A1 | 12/2004 | Hahnen et al. |
| 2007/0102473 A1 | 5/2007 | Shelton et al. |
| 2007/0125826 A1 | 6/2007 | Shelton |
| 2008/0172086 A1 | 7/2008 | Hillstead et al. |
| 2010/0170519 A1 | 7/2010 | Romo et al. |
| 2010/0175701 A1 | 7/2010 | Reis et al. |
| 2011/0027775 A1 | 2/2011 | Lu et al. |
| 2011/0155788 A1 | 6/2011 | Hillstead et al. |
| 2013/0006269 A1 | 1/2013 | Hillstead et al. |
| 2016/0235490 A1 | 8/2016 | Srivastava et al. |
| 2020/0093556 A1* | 3/2020 | Zemlok .................. A61B 34/35 |
| 2020/0093557 A1* | 3/2020 | An ......................... A61B 46/10 |
| 2020/0107895 A1* | 4/2020 | Hashimoto ............ A61B 34/35 |
| 2020/0360216 A1* | 11/2020 | Larkin .................. A61B 46/20 |

OTHER PUBLICATIONS

USPTO, Non-Final Office action for U.S. Appl. No. 16/521,500 dated May 21, 2021.

USPTO, Non-Final Office action for U.S. Appl. No. 15/885,792 dated Apr. 22, 2021.

\* cited by examiner

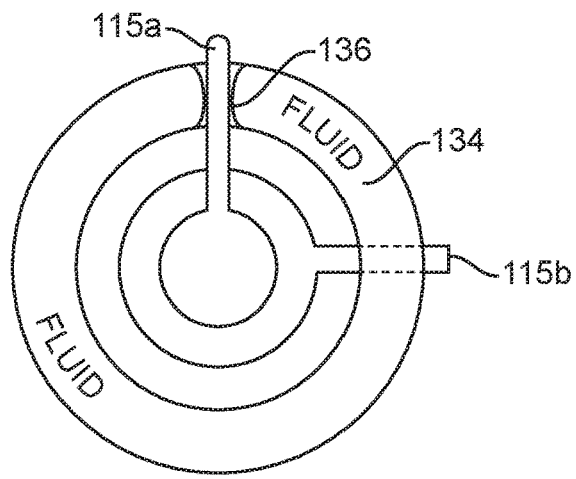
FIG. 10
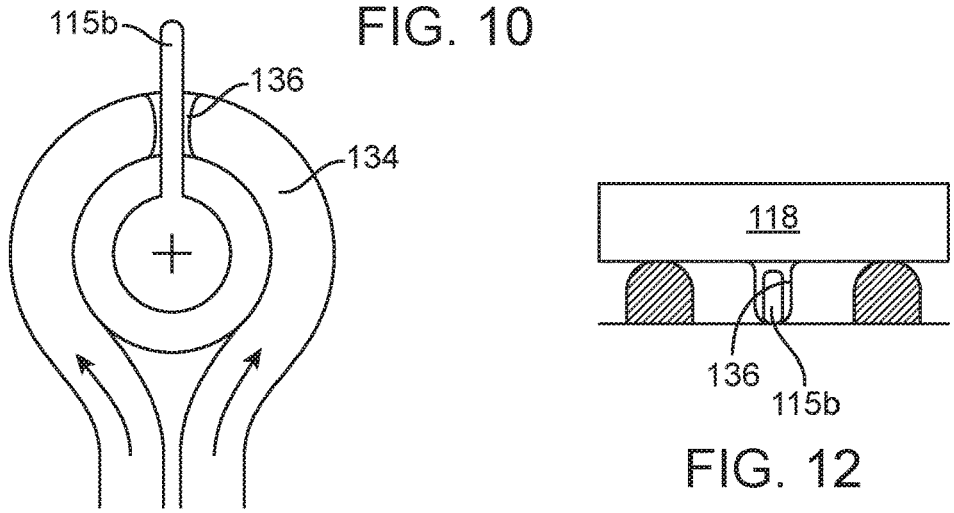
FIG. 11
FIG. 12
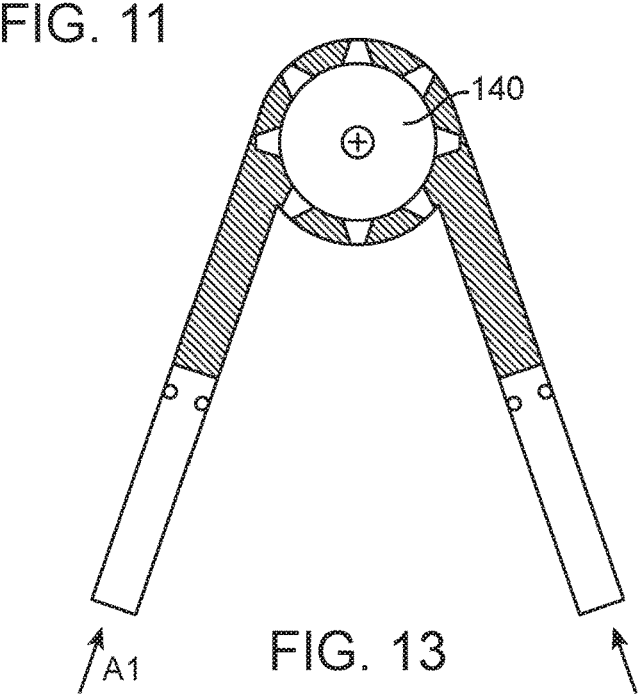
FIG. 13

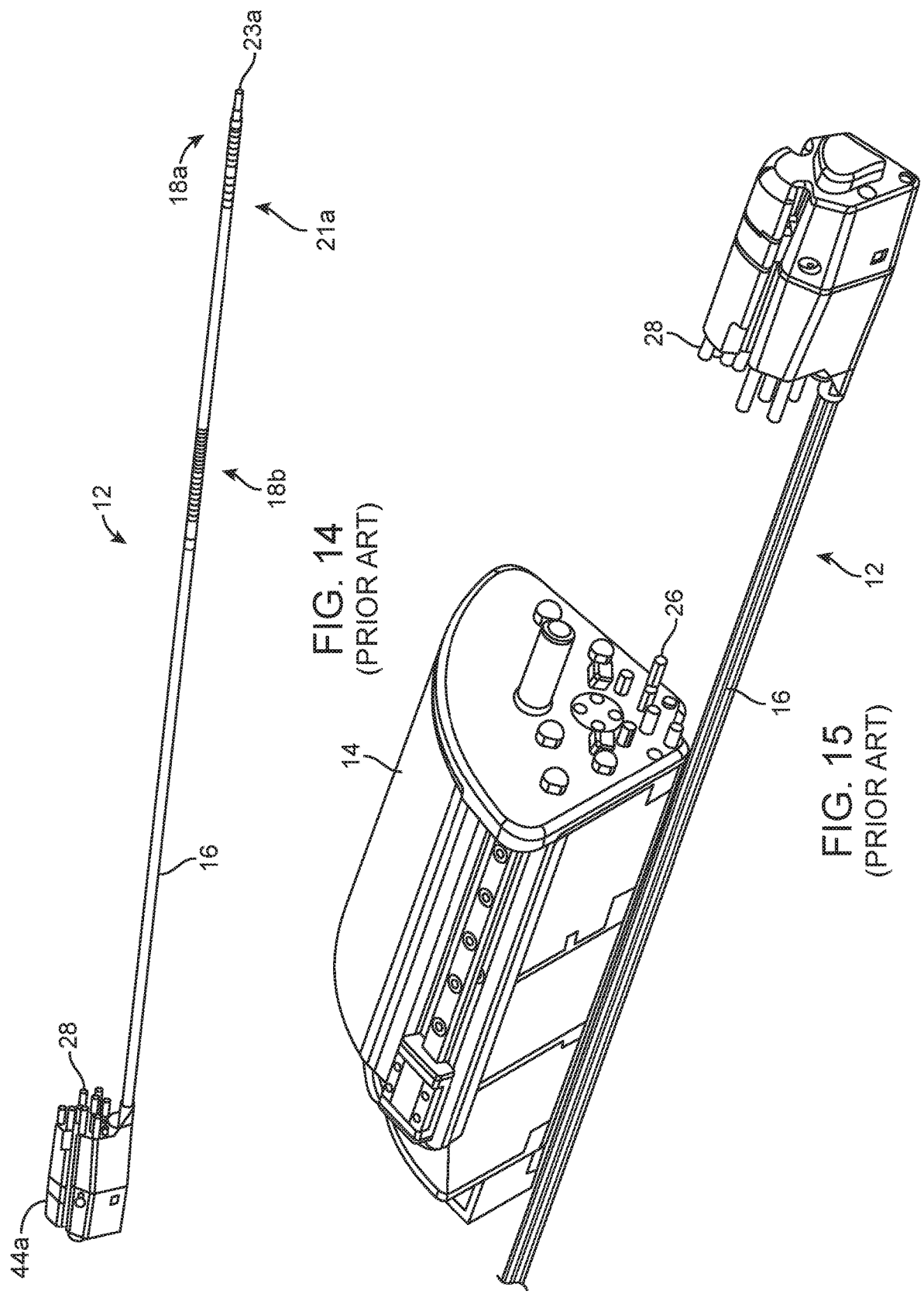

FLUID ACTUATION OF INSTRUMENTS THROUGH A STERILE BARRIER

This application is a continuation of U.S. Ser. No. 15/885,792 and claims the benefit of the following U.S. Provisional Applications: U.S. 62/452,953, filed Jan. 31, 2017; U.S. 62/452,950, filed Jan. 31, 2017; and U.S. 62/585,655, filed Nov. 14, 2017.

TECHNICAL FIELD OF THE INVENTION

The present invention relates generally to the field of surgical instruments and systems. In particular, this invention relates to fluid actuation and/or movement of surgical instruments or their end effectors.

BACKGROUND

Surgical systems used for robotically-assisted surgery or robotic surgery employ electromechanical drivers to drive movement of surgical devices within a body cavity, typically in response to signals generated when a user moves a user input device. The surgical devices may be surgical instruments having end effectors and/or they may be steerable lumen devices adapted to receive such surgical instruments.

One of the benefits of robotic assistance for minimally invasive surgery is that it enables the surgeon to control more complex and highly dexterous instruments with minimal mental and physical effort. In robotic surgery, the surgeon manipulates a master input device at a surgeon console to remotely operate instruments inside the patient. The signals from the input device are interpreted by the robot control system and used to drive mechanisms which move the instruments.

The gross motion of the instrument is typically achieved by a robotic manipulator arm which moves the entire instrument assembly in space. To supplement this gross motion, fine motion of the instrument tips is delivered through mechanisms which are built into the instruments themselves. In such systems, it is desirable to avoid the need to sterilize components housing motors and electronics. Instead, prior art surgical systems provide the driver (which houses the motors and some electronics) as a component on the manipulator arm that may be covered with a sterile drape in the surgical procedure room. The surgical instrument that is to be driven by the driver is a separate, sterile, component removably mounted over the sterile drape in a manner that allows the sterile drape to maintain a sterile barrier between the driver and the surgical device. Features are provided for transferring the mechanical output of the motors in the driver to the actuation elements in the surgical device, so that actuation of the motors causes the desired movement of the surgical device within the patient's body cavity.

Some prior art systems use rotary couplers for this purpose, to transmit motion from the robotic engine on the manipulator arm, through a sterile drape covering the arm, and into receiving couplers on the surgical instrument. In these systems, mechanisms inside the instrument convert this rotary motion into movements of the instrument end effector (jaw open close, articulation, etc.), typically using features such as wristed joints, articulating vertebrae, etc. In highly dexterous instruments such as high degree of freedom wristed instruments and fully articulating instruments for single-port surgery, an even more significant portion of the motion of the end effector is transmitted through the instrument via couplers.

In some cases, motors are built into the instruments themselves to control the instrument articulation, and driven using power received via an electrical contact in the drape.

Commonly owned, WO 2016/057989 (the '989 application), which is incorporated by reference, describes a surgical system that overcomes challenges of the prior art systems by eliminating the need for rotary coupling through the drape. That application describes a system that includes a drive unit on a support. The drive unit includes motors or other actuators and a plurality of output elements arranged such that operation of each drive unit linearly translates a corresponding one of the output elements. A surgical device has actuation elements extending through an elongate shaft to a distal articulation section, and an input subsystem carried at the proximal end of the shaft. Linear translatable input elements or pistons of the input subsystem are each associated with a corresponding one of the actuation elements. The input and output elements are positioned such that operation of an actuator linearly translates an output element, causing linear translation of a corresponding input element and engagement of an actuation element. A sterile drape is positionable between the input elements and the output elements. The described system thus allows use of a sterile drape without the requirement of special adapters or rotary couplers for transferring motion. Input devices operable by the surgeon allow a surgeon to provide input to the system for the purpose of driving the motors to move the surgical devices.

Some detail of the system described in the '989 will now be given, because that type of system may be configured to drive surgical instruments using the hydraulic system of the type described in this application. FIG. 14 shows a surgical instrument of the type discussed in the '989 application. The surgical instrument 12 is designed to be inserted through an incision (either directly or through a trocar or overtube) and positioned within a patient's body for use in performing surgery. The surgical instrument may be one having an end effector 23a that can be steered, articulated, and/or actuated (e.g. jaw opening and closing) having an end effector 23a, although it may be replaced with a steerable lumen device adapted to removably receive such surgical instruments. The surgical instrument includes actuation elements that, when pushed and/or pulled, cause active bending and/or articulation at the distal portion of the surgical device within the patient's body. The actuation elements extend through the shaft and are positioned to cause active bending/straightening of corresponding actively bendable sections, or articulation at joints or pivots, as the tension on the actuation elements is varied. The actuation elements are elongate elements (e.g. wires, rods, cables, threads, filaments etc.) having distal portions anchored to the shaft and proximal portions coupled to actuation mechanisms that vary the forces (tension or compression) on the actuation elements or the positions of the actuation elements. The actuation elements generally extend between proximal and distal directions.

The surgical instrument depicted in FIG. 14 includes an elongate shaft 16 having a rigid proximal portion. Towards its distal end there are one or more actively bendable or "steerable" sections 18a, 18b that bend in response to movement of the actuation elements. For example, steerable section 18a might be steerable in two degrees of freedom using steering actuation elements (e.g. three or four such elements) terminating at the distal end of the steerable section, and steerable section 18b steerable in at least one degree of freedom to move the distal end of the shaft laterally outward or inward in one degree of freedom using actuation elements, and which may be additionally moveable in a second degree of freedom. The numbers and combinations of actively bendable and jointed articulating sections, degrees of freedom, and actuation elements can be varied from what is shown.

FIG. 15 shows the instrument 12 spaced apart from a motor drive 14. Motor drive 14 houses the motors whose output is used to drive the actuation elements for the steerable and/or articulating sections, and/or for the opening/closing of instrument jaws, as applicable. The motor drive 14 is preferably supported on a support arm, robotic manipulator arm, or alternate support (not shown).

The motor drive 14 includes motors (not shown) and output elements 26, which in the drawing take the form of pins or posts. When the motor drive 14 and surgical device 12 are assembled, each such output element 26 is in contact with, coupled to, or engaged with a corresponding input element 28 of the surgical device 12, or otherwise positioned to cause each input element 28 to move in accordance with its corresponding output element 26. In preferred configurations, the input and output elements are on opposite sides of a sterile drape covering the motor drive 14 and the robotic arm, with the instrument 12 being removably positioned on the motor drive. This allows the instrument 12 to be exchanged with other sterile instruments during a surgical procedure while maintaining sterility of the surgical field.

The system may be set up so that the output elements 26 push the input elements 28 in response to motor activation, and/or so that the output elements pull the input elements 28. Each of the input elements corresponds to a degree of freedom of motion, or to end effector actuation, of the surgical instrument. The robotic system controllers activate motors of the motor drive 14 in response to surgeon input at the input device to cause movement of the output elements 26 so as to produce the desired movement, articulation or jaw actuation of the instrument.

Commonly-owned application WO/2017/181153 describes ways in which the linear drive can be used to effect an axial roll of the instrument.

BRIEF DESCRIPTION OF THE DRAWINGS

FIGS. 8-12 illustrate configurations for transferring force and motion through a surgical drape using hydraulics.

FIG. 13 shows a configuration for transferring force and motion using hydraulics to effect instrument roll.

FIG. 14 illustrates a prior art surgical instrument for a robotic-assisted surgical system.

FIG. 15 illustrates the instrument of FIG. 14 in exploded view with a motor drive for actuating movement of the surgical instrument.

DETAILED DESCRIPTION

This application describes a robotic-assisted surgical system incorporating a hydraulic surgical end effector drive system 10 (HSEEDS), a system in which fluid is used to transfer motion and force to instrument end effector. In general, this concept uses pressurized fluid (either gas or liquid) to impart motion and force on the instrument end effector. It is understood that this concept applies both to single-site surgical robotics as well as multi-port applications. This application discusses a system in which the fluid subsystem is a part of the surgical instrument, and also a concept in which the fluid subsystem is a part of the drive system used to provide input forces and motions to the surgical instrument. As both subsystems are covered in this disclosure, the HSEEDS invention consists of a complete drive system in which one or both subsystems are achieved using fluid to transfer forces.

The embodiments discussed in this disclosure focus on mechanisms to transmit linear motion, such as is described in the '989 application, but it is understood that this invention would also apply to similar mechanisms which utilize rotary motion which are also driven by fluid pressure (for example using rotary hydraulic actuators). The drive system may control the motions of the mechanism by controlling the fluid pressure directly, by controlling the position of an input drive mechanism (such as an input piston) directly, or by monitoring and controlling both position and pressure. To simplify the discussion, this application refers to this system as a "hydraulic" instrument drive system, with the understanding that the fluid being used in the system may be either a liquid or gas. There are some differences in system design and analytical complications between a liquid system and a gas system, which are discussed briefly at the end of this application.

Figure 1:
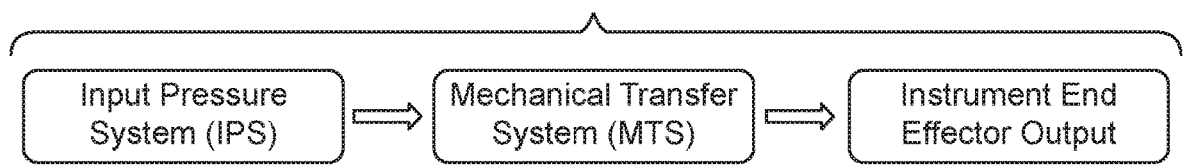
FIG. 1 schematically illustrates subsystems of a hydraulic surgical end effector drive system.

The HSEEDS 10 consists of three subsystems, the input pressure system (IPS) 12, the mechanical transfer system (MTS) 14, and the instrument end effector output system 16 (IEEOS) as schematically depicted in FIG. 1. In the system 10, the IPS 12 and/or the IEEOS 16 are driven using a fluid system. One may be mechanical or electromechanical, but at least one is driven hydraulically. In the case of a fluid IPS, the IPS delivers and regulates the fluid pressure delivered to each input mechanism of the MTS. The MTS then transfers this fluid pressure and motion to the input side of the IEEOS, and the IEEOS converts these input forces and motions into motions and forces of the instrument end effector tips. The IPS referred to in this disclosure could be designed and built in a number of different ways, but two potential embodiments are discussed below.

Figure 2:
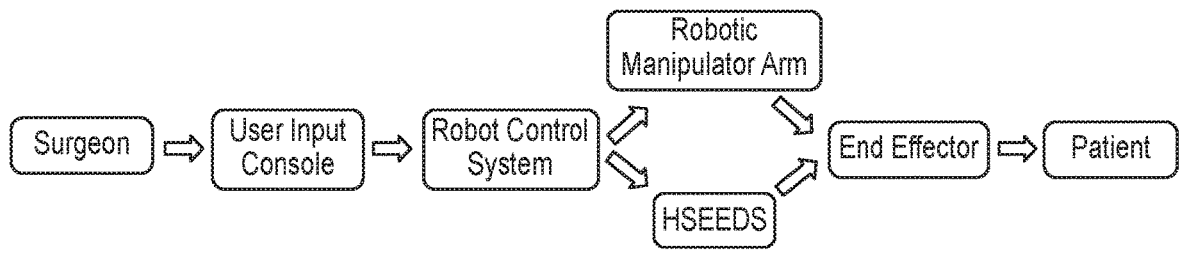
FIG. 2 is a block diagram schematically illustrating components of a robotic surgical system employing the hydraulic surgical end effector drive system of FIG. 1.
Figure 3:
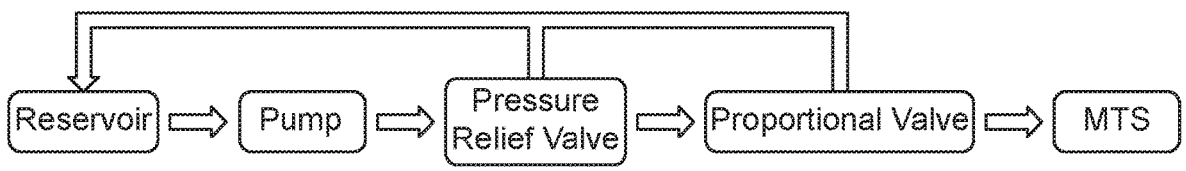
FIG. 3 schematically illustrates elements of the input pressure system of FIG. 1.

The system may be incorporated into a robotic surgical system as schematically depicted in FIG. 2. A surgeon provides input to the system via a user input console. A robot control system generates instructions based on the user input in order to control the robotic manipulator arm for certain types of instrument movement, such as gross motion of the instrument, and to control the HSEEDS system which effects finer motion of the instrument, such as shaft articulation or bending, wristed motion of the end effector, jaw actuation, etc.

The Input Pressure System (IPS)

A first embodiment of an IPS includes individual electrically powered and controlled dynamic pumps (such as centrifugal pumps or axial-flow pumps or equivalent) to provide pressure to each degree of freedom of the MTS. For example, each pump could be dedicated to manipulating one input of the MTS of a linear push-push instrument drive mechanism such as that described in WO 2016/057989. If enough pushing and pulling force is required, two pumps may be needed for each degree of freedom of the MTS so that a double acting piston can be used to both push and pull.

This could also be achieved with a single pump if a mechanism such as a valve is used to direct the pressurized flow to either side of the double acting piston. Also, in the push-push system described in this disclosure, pull forces are not needed and therefore a single acting piston would suffice. Double acting pistons would be part of the MTS and are discussed in the MTS section below. The IPS subsystem may consist of a main fluid reservoir or tank, a hydraulic accumulator, one or more filter assemblies, electrohydraulic servo valves or proportional valves, pumps, pressure relief valves, flowmeters, temperature sensors, heat exchangers, etc. In one embodiment, each pump may draw fluid from a main input reservoir and supply pressurized output fluid to the MTS input. The pressure, flow rate, and position of the flow to the MTS may be controlled by the robot control system using a servo valve, proportional valve, or similar. Alternatively, these flow conditions provided to the MTS from the IPS could be controlled and monitored using flow control valves, pressure relief valves, flowmeters, temperature sensors, pressure transducers etc. The fluid may be transferred from the IPS to the MTS through flexible or rigid tubing, piping, or internal passages.

An alternative concept for a hydraulic IPS uses electromechanical actuators and motors (or equivalent) to drive positive displacement pumps (such as a piston or plunger) to control the position and pressure of each degree of freedom of the MTS. This would share many of the benefits of the first embodiment, but could be realized with fewer hydraulic components, a more familiar electromechanical input system to the hydraulic drive, and potentially less noise and power consumption depending on the type of dynamic pump used in the first concept described. This IPS with positive displacement pumps driven by electromechanical actuators may still use pressure transducers, temperature sensors, etc. for input into the control system. Also, it is likely that a pressure relief valve will be integrated as a failsafe into the output side of the pump to avoid excessive pressure if there is a failure in a sensor or the control system. For this type of system, the input position of the piston (or positive displacement pump) can be commanded directly to control the position of the inputs of the MTS. Because this is not a dynamic pump and the hydraulic portion of the system is likely "closed" (without the reservoir of the first system), effective sealing must exist to prevent leaks and/or a reservoir must exist with a mechanism to maintain or refill fluid in the line either during use or between uses.

Using a hydraulic IPS can provide some advantage over prior art systems. First, flexible tubing can enable improved form factor design by positioning the IPS in a more favorable location in the robotic surgical system without the need for a drive system built directly adjacent to the MTS. For example, in previous push-push system designs, the motor packs, gearing, and linear actuators are all mounted in series along the pin axis. This results in significant weight and volume of mechanisms out near the instruments at the end of the robotic manipulator arm. Using a hydraulic IPS as part of this HSEEDS invention enables the IPS to potentially be positioned in the base of the robotic manipulator cart rather than mounted to the manipulator itself. Hydraulic flexible tubing can be routed through the center of the robotic arm. This would enable smaller, lighter, manipulator arms which occupy less space around the surgical site. Additionally, moving the pumps or drive engines into the base of the arm makes heat removal much simpler, and also enables the use of larger motors at more optimal operating points. This should reduce overall heat generation, simplify cooling, and use less power.

Another advantage to using a hydraulic IPS is the ability to obtain haptic information, which can be used to provide feedback to the surgeon, without integrating separate and expensive load cells. Using a pressure transducer in the tubing on the output side of the IPS, the control system can monitor the pressure, and therefore force or torque being applied to the instrument mechanism. The pressure on each degree of freedom of the IPS will tell the control system the forces on each input mechanism to the MTS. Assuming an MTS design that is relatively low friction and back drivable, these measured forces will be proportional to the forces being applied to the instrument degrees of freedom. As such, the pressures measured at the IPS can be used to calculate surgical forces such as jaw open-close, forces in X, Y, Z, and moments about X, Y, Z, depending on the degrees of freedom of the instrument in use.

The Mechanical Transfer System (MTS)

Accepting the output of the IPS is the MTS for which a number of different mechanisms could be used. In this disclosure, the MTS is described as the mechanical system used to transfer the hydraulic input forces and motions from the IPS, to the instrument input mechanism in a useful way. Essentially, the MTS converts the pressure and motion of the fluid to motion that can be accepted by the instrument. As previously discussed, this disclosure focuses on axial motion for a push-push instrument mechanism, but rotary motion or other motion is also feasible with a hydraulic system.

A first concept uses a piston, actuated along an axis by the fluid pressure, and utilizes a sliding sealing interface to maintain fluid pressure as the piston moves. In this design, the relationship between speed and force of the MTS vs the speed and force generated by the pump in the IPS can be controlled by the pressure area of the pistons in the MTS. This is very analogous to gear ratios in a purely mechanical system. Consider the second IPS concept. If the area of the MTS piston is 2× larger than the area of the plunger in the IPS, the force exerted on the MTS will be 2× the force applied to the plunger of the IPS. Also, if the IPS plunger moves a certain distance (at constant pressure), the MTS piston will move ½ the distance. These ratios can be controlled in the mechanical design to optimize the relationship between input forces and speeds to output forces and speeds. A more complex mechanism could also be designed which could dynamically change the pressure area one or more of the pistons enabling the control system to modify the input/output relationship based on the type of instrument being used or the demands of the surgeon, application, or conditions. This type of transmission system could be designed with discrete steps or nearly continuous ratios. Another consideration for this piston system is that it may be necessary to use double acting pistons to achieve the required push and pull forces demanded to manipulate the instrument end effector under load. With these double acting pistons, it may be useful to have two pumps for each degree of freedom of the MTS, one to apply pressure on one side of the mechanism and one to apply pressure on the other. Alternatively, a spring can be used in the piston to provide pull force when the IPS relieves pressure. This would enable a single pump in the IPS per degree of freedom in the MTS. Also, with a push-push system pull forces are not needed as each pin is only used to push.

A second concept uses a flexible membrane, such as a bellows, to extend along an axis under pressure, which would be completely closed and therefore would not require any sliding seals in the MTS. In this design, pressure from the IPS pressurizes the inside of the bellows which then expands axially to move and exert force on the input mechanism of the instruments. Similar to the double acting piston concept, the bellows concept could be applied to exert higher push and pull forces by using a dual bellows concept for the MTS with 2 input pumps in the IPS for each degree of freedom of the MTS. One bellows is pressurized for push, and one for pull. Alternatively, a single bellows may be feasible by designing a nominal spring force into the bellows system to exert pull force when pressure is reduced at the IPS.

The Instrument End Effector Output System (IEEOS)

The IEEOS transfers motion from the MTS to the instrument end effectors. In prior art, this is typically achieved with cables or rods which are actuated by rotary or axial motion imparted to the instrument from the motorized robotic engine at the end of a robotic manipulator arm. The HSEEDS invention may be realized with either a prior art mechanical instrument system or with a hydraulic IEEOS. In this hydraulic IEEOS, input motion from the MTS is transmitted to the end effector by hydraulic lines inside the instrument. The fluid used for the hydraulic actuation is contained inside the instrument tubing and is fully sealed.

This concept does not need much explanation beyond that provided in previous sections. For a hydraulic IEEOS, the force and displacement of the MTS provides the input to the hydraulic lines inside the instrument which in turn pass this energy to the instrument end effector. On the input side of the IEEOS, pistons or a bellows can be used to engage with the MTS and transfer the motion and force of the MTS to the motion and pressure of the hydraulic lines. On the output side at the instrument end effector, a mechanism is used to again convert this pressure and motion of each hydraulic line into mechanical motion of the degrees of freedom of the instrument end effector (such as a wrist, jaw open-close, etc.). Depending on the desired motion of the end effector, a number of mechanisms could be used to transform the hydraulic input to mechanical output such as a piston, bellows, rotary hydraulic actuator, etc. These mechanisms may then either directly connect to the instrument end effector or connect to cables or rods which ultimately impart the motion to the instrument tips. Similar to the description of the hydraulic IPS, the hydraulic IEEOS offers advantages to prior art such as the ability to further separate the input and output mechanisms of the instrument (i.e. so it does not have to be physically in-line), and use input and output pressure area ratios as a method of scaling the relationship between input and output forces and displacements. Perhaps even more importantly, a hydraulic IEEOS could be capable of significantly higher forces than prior art systems, as compression of fluid can withstand greater loads than tension in thin wire cables. This could be useful for more complex instruments such as staplers, or in applications requiring strong jaw forces such as suturing. Again, pressure transducers could be used to measure pressure in each line of the IEEOS to give force information to be used for haptic feedback, as described in previous sections in more detail. Lastly, a hydraulic IEEOS can include fail safe measures which reduce the chances of catastrophic failure. By including pressure relief valves, excessive forces can be limited by ensuring that at a certain maximum level, fluid is released from the line and the pressure is released. To prevent contamination, this could easily be released by the valve into an internal reservoir to prevent leakage outside of the instrument box. This could be useful to prevent irreversible failure during use and also for emergency situations that could require the user to overpower the instrument to move it into another pose. Also, if the overloading failure is a loss of fluid pressure, instrument maintenance may be possible enabling longer life and more uses per instrument. Rather than cables yielding and needing to be replaced (which causes instruments to be disposed of in lap instruments today), the released fluid can simply be replaced to refill the hydraulic lines and regain performance as when the instrument was new. This could reduce per procedure costs by enhancing reliability and reuse counts.

Gas vs. Liquid

As mentioned previously, this concept could be realized with either gas lines (for example air), or liquid lines (such as water, mineral oil, hydraulic fluid, etc.). Prior discussion in this disclosure focuses mostly on liquid systems but the same principles apply in the case of gas. Air may seem to be an appealing choice for these applications because of the abundance of availability in the OR. A main reservoir may not be needed if filtering is either not required or done at the inlet of the system, and system leaks are less likely to cause damage to other components in the system or create new hazards in the OR. However, other risks, analytical challenges, and mechanical design difficulties counteract these initially perceived benefits.

The biggest issue with a gas system is compressibility. Gas is much more compressible than liquid, and therefore when pushing a piston, the system will need to travel significantly further to exert the same pressure in a gas system compared to a liquid system. This causes additional challenges for the mechanical design as more travel must be accommodated by the system and inefficiencies in a pneumatic system require higher input forces to achieve comparable output forces. For pneumatic systems, pumps typically must run constantly to hold pressure and position where hydraulic systems do not. As a result, pneumatics lead to less efficient operations causing more difficult mechanical design constraints such as higher forces, greater heat generation, larger pumps, and larger mechanisms than comparable hydraulic systems. To further complicate the mechanical system, air has a higher bulk modulus which can be dangerous if there is a failure at high pressure. Because of this modulus and compressibility, high pressure failures have significant potential energy that can result in explosive failures in improperly designed systems. Therefore, additional measures must be taken to ensure safe design and operation in certain types of pneumatic systems.

Compressibility and inefficiencies also complicate the control system of the robot. Because of these system losses, the relationship between input forces/motions and output forces/motions becomes non-linear. This makes the design of a predictable and precise control system much more difficult and likely would also lead to more sophisticated sensing requirements for the mechanical system. For example, at relatively low pressures, a hydraulic system can be assumed to be approximately incompressible. This simplification enables separation between pressures and positions. However, in pneumatics with compressible gases, the pressure must be known by the system to determine the position of the end effector since the density of the gas is variable. These complications make it more difficult to transmit motions and forces through long pneumatic lines than hydraulic lines and reduce some of the benefit of this invention over prior art.

As a result, the focus of this disclosure is on a truly hydraulic surgical end effector drive system (HSEEDS) due to the apparent advantages. However, it is understood that pneumatics are also feasible.

Non-limiting examples of subsystems suitable for use with the system described above will next be described.

Figure 4:
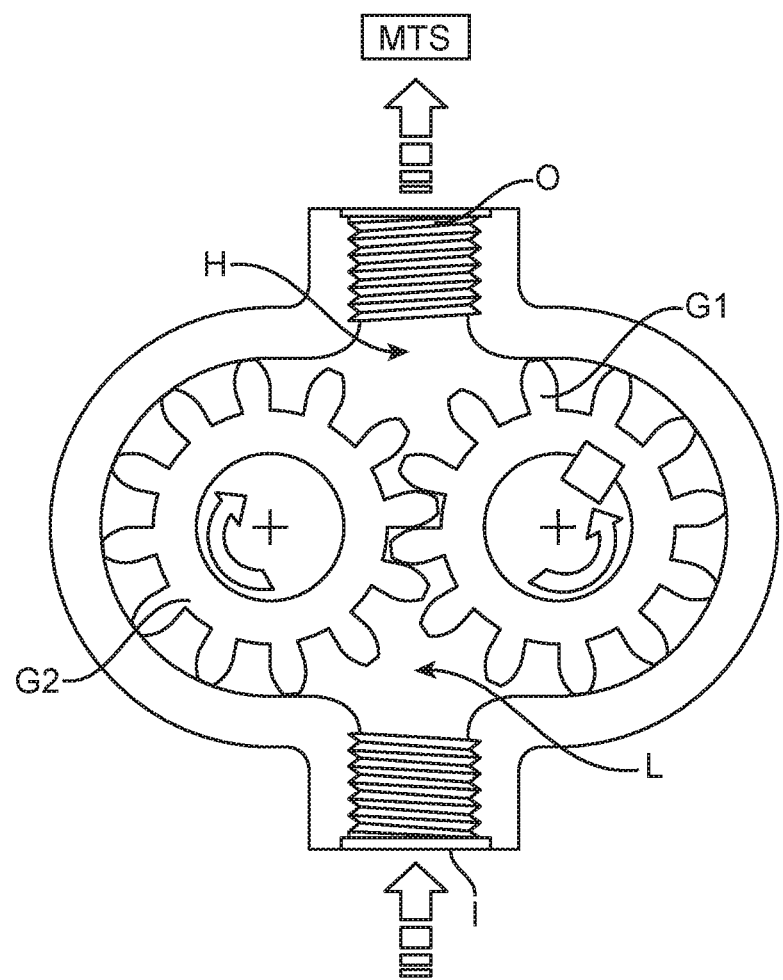
FIGS. 4-6 give examples of pump configurations that may be used for the input pressure system of the system of FIG. 1.

FIG. 4 shows a gear pump which may be used as an IPS of the disclosed system. The gear pump uses meshing spur gears G1, G2 to pull fluid from a reservoir into the pressurized volume via inlet I. Gear G1 is driven by a motor, while gear G2 is moved by the teeth of gear G1. A low-pressure area L pulls fluid in from a reservoir and a high-pressure area H pressurizes a fluid volume to perform some desired task. The pressure in both areas can be monitored to provide force feedback information if desired.

In this application, the pressurized volume is connected via outlet O and a hydraulic line to the MTS, which may be a drive piston that will transmit linear motion at the drape where it can be received by a corresponding driven piston on the opposite side of the drape. As the motor pushes fluid into the pressurized volume, the drive piston responds to the higher pressure by extending towards the MTS. When the piston encounters force, the pressure in the pressurized volume will increase. This increased pressure may be detected by pressure sensors and communicated to the user to indicate, for example, forces encountered by the surgical instrument as it moves through the motion resulting from the piston motion (e.g. instrument contact with tissue during movement, jaw closing forces). Representations of the force feedback may include visual or auditory feedback, or delivered as force feedback on control handles used by the surgeon to cause movement of the surgical instrument.

It should be noted that in this embodiment, a hydraulic fluid is selected to have sufficiently high viscosity so that it does not seep around or escape the meshing gear teeth. Additionally, the motor may be designed to allow pressure above a certain level to back-drive the position of the motor, and as a result the linear translating pin/piston.

Figure 5:
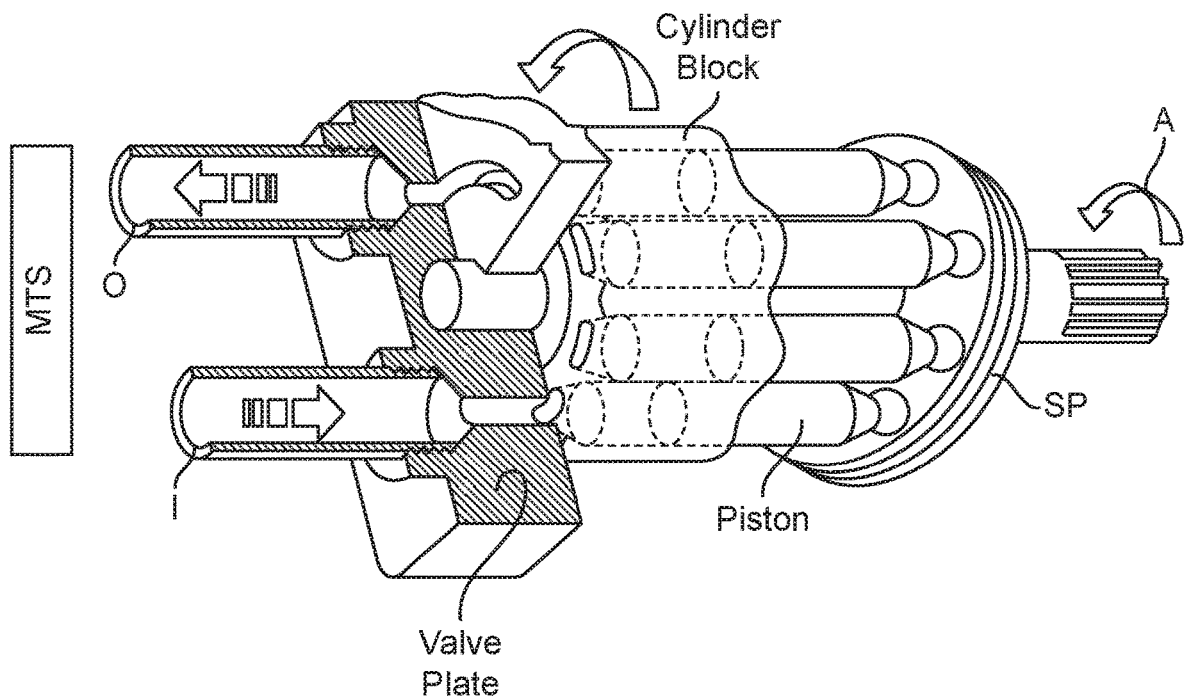

A second example of an IPS utilizes a swashplate configuration as shown in FIG. 5. As the motor turns the swashplate (depicted by arrow A), the swashplate pushes and pulls on the pistons within their cylinders. Pulling on a piston creates a vacuum that is filled by fluid in the low-pressure reservoir and pushing on the piston sends that fluid to the high-pressure area to exert force towards the instrument. This force may be used by the MTS, for example, to drive a drive piston of the type described in the '098 application.

Figure 6:
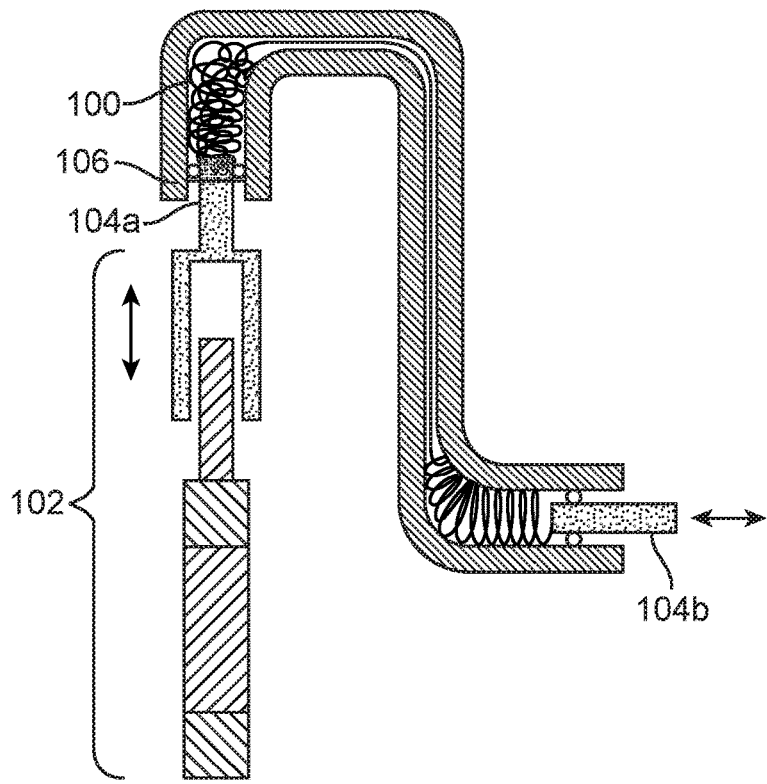

A third embodiment shown in FIG. 6 includes a pump that uses an enclosed fluid volume in a chamber 100 defined by a flexible or rigid fluidic channel. The rotation of the motor (not shown) is converted to linear motion, for example with a ball screw of a linear actuator 102. A pin 104, sealed within the chamber 100 by an o-ring seal 106, reciprocates within the chamber, pushing and pulling an enclosed volume of fluid back and forth, which displaces a second pin 104b that serves as an output pin (MTS) at the drape interface.

Pump Positioning

In preferred embodiments, the system is configured so that the output from the MTS is located at the distal end of the robotic arm. The distal end of the arm is then covered by a sterile drape, and a removable surgical instrument is mounted to the arm so that its input elements for articulation, actuation etc. of the instrument may be driven through the drape by operative elements of the MTS.

Figure 7:
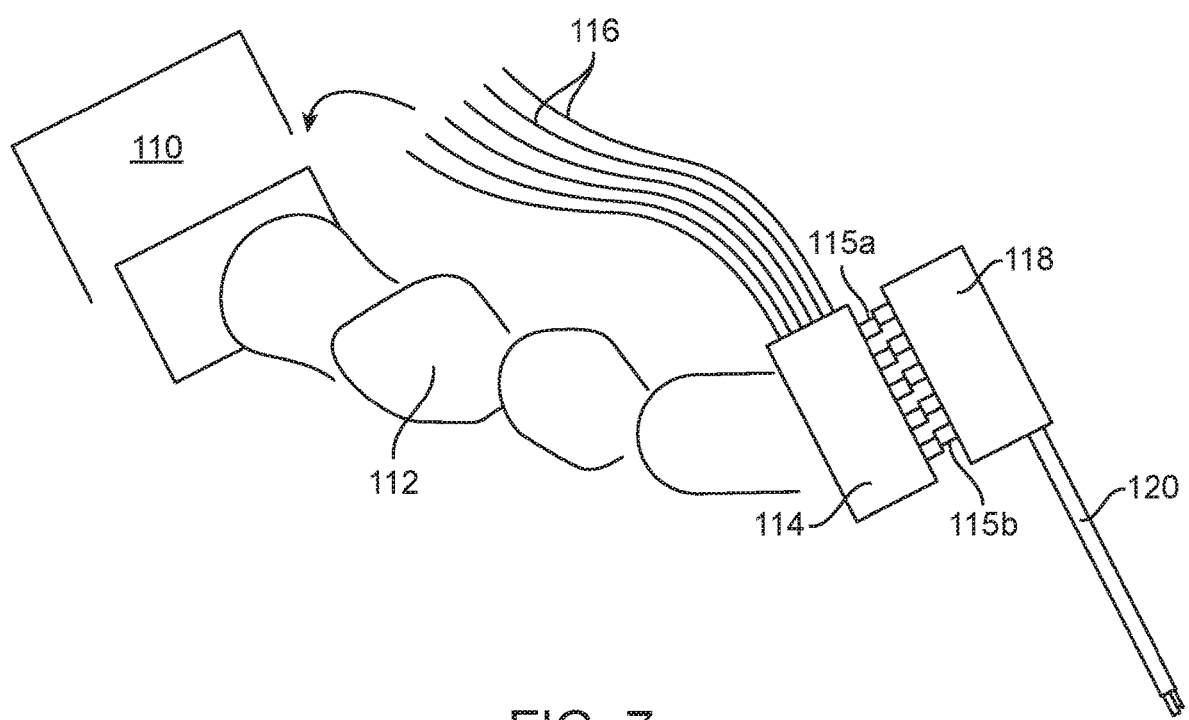
FIG. 7 illustrates one configuration of a hydraulic surgical end effector drive system incorporated into a surgical robotic system.

Systems incorporated the hydraulic system may position the pump at a variety of locations relative to the site where motion is transferred between the drive components at the drape and the driven components of the instrument. One option is shown in FIG. 7, which shows a base 110 supporting an arm 112 such as a robotically and/or manually moveable support arm for a surgical instrument. The base may be a cart positioned on the floor, or it may be mounted to the surgical bed, the ceiling of the operating room, etc. In a more conventional surgical system, motors would be carried by the arm, such as in the housing or region 114 (also referred to in this application as the "engine"), adding significant weight to the arm.

In this embodiment, the hydraulic lines 116 extend from a series of pumps in the base 110 or cart to the housing or region 114 in which the MTS, such as pistons 115a (or rotary elements) driven by the pumps transfer motion through the drape (not shown) to the associated driven components 115b on the other side of the drape. These components 115b extend from a proximal housing 118 of the surgical instrument 120.

In other embodiments, the hydraulic pumps are disposed distally on the arm, such as inside the housing 114, allowing shorter hydraulic lines to be used than described in the previous embodiment. For example, shorter flexible hydraulic lines may connect the pump to the linear drive pin. Alternatively, hydraulic lines may be molded or machined paths in a manifold. A preferred manifold is configured to enable optimal placement of the motors relative to the linear translation pistons disposed at the drape such that the overall size and mass of the engine is minimized.

The pressure inside the contained volume of fluid can be monitored via pressure sensors and that information fed back to the user interface to inform the surgeon of the forces applied to the tissue. The lengths, diameters and shapes of the hydraulic lines are preferably equivalent such that fluid flow through one line is equivalent to fluid flow in all the others.

Hydraulic Drape Manifolds

Figure 8:
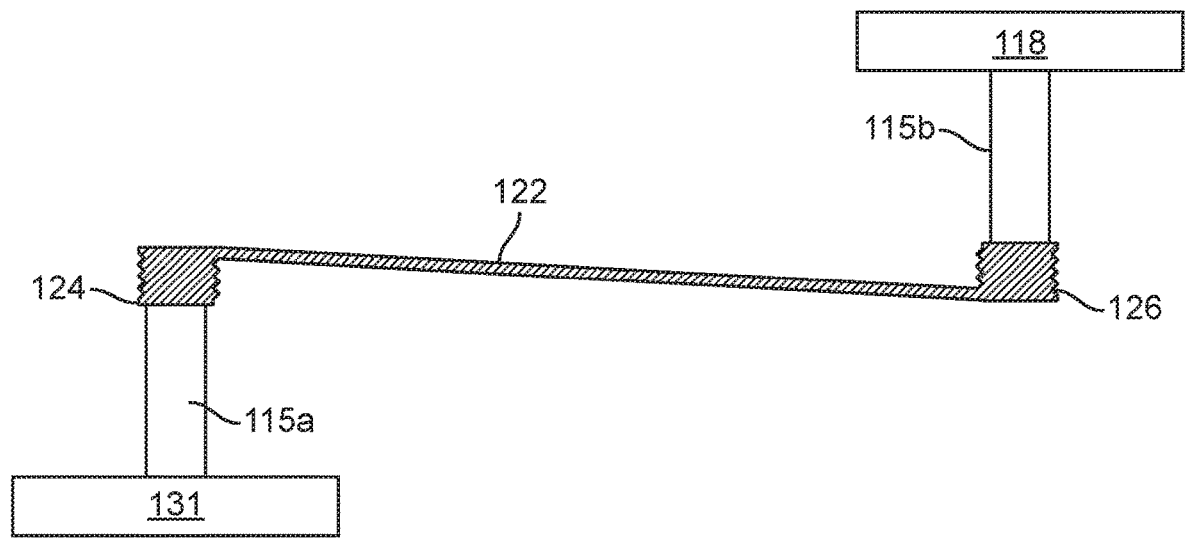

Referring to FIG. 8, in some embodiments some MTS features for force and motion transfer may be built into the drape that is positioned between the instrument and the engine. This would enable the motor motion to occur in a location that is remote to the instrument actuator. The drape would include a manifold of hydraulic lines 122, each hydraulic line having a proximal 124 and distal 126 end. The proximal and distal ends are compressible and extendable such that compression of the proximal end 124 resulting from output from a piston 115a driven by the system's driver 131 (i.e. whether that driver be an IPS as described above or a more conventional motor system as discussed in the '989 application) creates extension of the distal end 126. Extension of the distal end 126 drives a piston 115b operatively coupled to an actuator of the instrument 118. In this manner, the engine can apply compression to the drape in one location and have the motion carried by fluid to another location in the drape to drive a mechanism in the instrument. The compressibility/extendability of these motion-coupling features 124, 126 of the hydraulic lines may come from elastic properties of the material and/or expandable mechanical features such as bellows.

Figure 9:
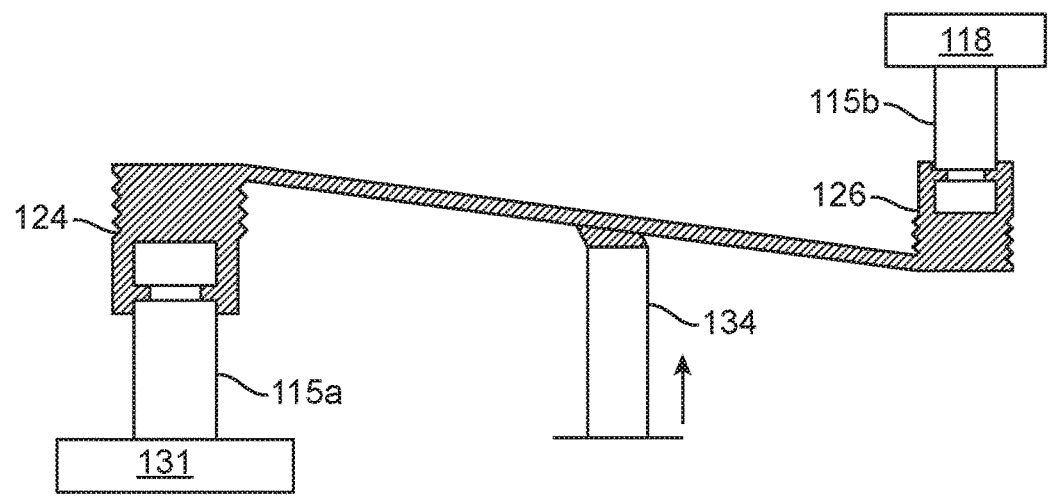

FIG. 9 shows a modified version of the previous embodiment, in which the drape manifolds include a third compressible location where an action during loading an instrument onto the robotic system would create a physical engagement between the motion-coupling features 124, 126 of the drape manifold and the corresponding engine drive pin/pistons and driven instrument pistons at the ends of the hydraulic line. For example, the motion-coupling features may be shaped to capture the corresponding pins and to securely retain the pins once they have been expanded. In the illustrated example, the driver pin and instrument pin each have recesses built into their external surface as shown, so that during instrument insertion the engine and instrument pins can nest with the compressible/extensible portions of the drape manifold. When the manifold is compressed in a third location (such as by the post 134 in FIG. 9), fluid is driven to the compressible extensible portions of the manifold 124, 126, inflating them and thus causing them to engage with the instrument and engine pins. This could be particularly useful in push/pull applications, i.e. where the driven pin is actively driven in both inward and outward directions for instrument operation, so that one drive pin/piston could both push and pull on the driven piston of the instrument (input pin) pin to create desired action. An advantage for this particular method of engaging push and pull is the zero-backlash nature of the engagement due to the conformity of the hydraulics to the pin shape. This could eliminate backlash due to part tolerancing, for example.

A similar embodiment is represented in FIG. 10, except that in this embodiment the hydraulic drape manifold enables rotary motion at the drape interface—where rotary motion from the driver (e.g. rotary output from a motor) is transferred to rotary motion at the motion input for the surgical instrument. In the example, the hydraulic drape manifold is an annular fluid-filled element 136 (or "donut") in the drape. The annular element 134 has a radial opening 136 that seats around an engine output mechanism or actuator in the form of a wiper 115*a*. The instrument attaches to the drive assembly (above the drape) in such a way as to align a second wiper 115*b* with the donut, the instrument wiper being rotationally offset relative to the engine wiper actuator. This instrument attachment could constrain the shape of the fluid-filled drape donut in such a way as to not allow any expansion of the donut size. As such, if the drape donut cannot expand, movement of the driver wiper 115*a* rotationally around the drape donut would cause movement of the wiper 115*b* of the instrument attachment due to the volume of constrained fluid between the two blades. Motion can be transferred in either clockwise or counterclockwise directions due to the constrained fluid volume between blades in either direction.

Referring to FIGS. 11 and 12, a similar embodiment to the donut may consist of a fluid filled annular channel formed of an inelastic material. The channel is fluidly coupled with an inlet and outlet loop for the hydraulic fluid. In this embodiment, there is not a driver wiper actuator, instead the hydraulic pump is fluidly coupled with the loop of the inlet and outlet but is positioned in a physically remote location (which may be one of the locations discussed with regard to FIG. 6. An instrument wiper 115*b* is positioned in the radial opening 136. Fluid pumped into one side of the channel would displace the instrument wiper 115*b*, causing it to move with rotary motion in a first direction. Fluid pumped into the opposite side of the channel would move the wiper in the opposite direction.

In alternative embodiments, hydraulic manifolds and constructed into the drape and fluidly coupled to hydraulic pumps positioned remote from the drape. Such manifolds might include motion coupling features such as fluidly driven pistons, or compressible/expandable drape features of the type described above, that are engaged with or coupled to input pins or other input features of the surgical instrument.

As discussed above, a hydraulic system may be used as an actuator within the instrument itself. In one embodiment, a hydraulic line extends down the instrument shaft to the end effector (e.g. a jaw). Pushing or pulling on the column of water within the hydraulic line could cause the jaw to open or close.

In another embodiment, a hydraulic drive may also be implemented for axially rotating (or "rolling") the instrument. In this embodiment, the surgical instrument is fixed to a gear or splined shaft 140 that is tightly constrained, much like the rotary pump described in the FIG. 4 embodiment. See FIG. 13. In this embodiment, pushing fluid at one side of the splined shaft would cause rotation of the spline in the direction of applied pressure. For example, fluid pushed on the arrow A1 in FIG. 13 would cause clockwise rotation of the spline and corresponding rotation of the instrument shaft in a first direction. Pushing fluid on the opposite side (A2) would cause the opposite rotation of the spline and instrument shaft. This may be particularly useful if there is not space for a belt or gear at the instrument shaft to transfer the rotary motion from the instrument actuation interface. Hydraulics could take up less space in that volume, but still be capable of applying the same torque to the roll shaft. Additionally, hydraulics could be a mechanism for scaling the rotation relative to the linear translational input. For example, the diameter of the piston can be sized, relative to the volume of fluid captured between the fins or gear teeth on the driven pinion, such that 10 mm of stroke on the piston created greater than 360 degrees of rotation on the pinion. Alternatively, 10 mm of stroke could be 180 degrees rotation, or 720 degrees. The relationship between the diameter of the piston and the diameter and captured volume of the pinion are used to determine the force and displacement characteristics of this system.

It should be appreciated that although the various embodiments are described in the context of robotic surgical instruments, it should be understood that the described concepts for effecting motion of a surgical instruments might also be used for instruments such as hand instruments that are not part of a robotic surgical system.

All prior patents and applications referred to herein, including for purposes of priority, are incorporated herein by reference.

We claim:

1. A surgical barrier for covering a non-sterile component of a surgical system and for transferring motion between a drive system of the non-sterile component and a surgical instrument, wherein the drive system is of a type including a drive member, and the surgical instrument is of a type having at least one mechanical instrument actuator moveable to cause a movement of the surgical instrument, the surgical barrier including:

a surgical drape including a first surface and a second surface opposed to the first surface, the surgical drape removably positionable covering a non-sterile component of a surgical system with the first surface contacting a drive member of the non-sterile component and with the second-surface contacting at least one mechanical instrument actuator of a surgical instrument;

the surgical drape further including at least one manifold disposed between the first surface and the second surface, said manifold containing a volume of fluid, the manifold shaped such that movement of the drive member deforms at least a portion of the first surface, driving the volume of fluid through the manifold in a first fluid direction to deform at least a portion of the second surface to thereby move the mechanical instrument actuator contacting the drape and cause movement of the instrument.

2. The surgical barrier of claim 1, wherein said at least a portion of the second surface is expandable such that driving the volume of fluid through the manifold in the first fluid direction expands said at least a portion of the second surface.

3. The surgical barrier of claim 2, wherein said at least a portion of the second surface is a bellows configured such that driving the volume of fluid through the manifold in the first fluid direction expands the bellows.

4. The surgical barrier of claim 1, wherein said at least a portion of the second surface is an elastic portion such that driving the volume of fluid through the manifold in the first fluid direction in the first fluid direction elastically expands the elastic.

5. The surgical barrier of claim 1, where said at least a portion of the second surface is a piston at least partially disposed in the manifold.

6. The surgical barrier of claim 1, wherein said at least a portion of the second surface is engageable to the at least one mechanical instrument actuator.

7. The surgical barrier of claim 1, wherein the manifold is an arcuate manifold, and wherein the first fluid direction is a circumferential direction.

8. A surgical barrier for covering non-sterile components of a surgical system, including:
   a surgical drape including a first surface positionable covering a non-sterile component of a surgical system and a second surface opposed to the first surface;
   a surgical instrument having at least one mechanical instrument actuator positionable in contact with the surgical drape, the at least one mechanical instrument actuator moveable in a first mechanical instrument actuator direction to cause a first movement of the surgical instrument;
   the surgical drape including at least one manifold, a volume of fluid disposed within the manifold, and an output member at least partially disposed in the manifold, the manifold shaped such that driving fluid through the manifold in a first fluid direction drives the output member in contact with said mechanical instrument actuator to advance said mechanical instrument actuator in a first mechanical instrument actuator direction causing movement of the instrument.

9. The surgical barrier of claim 8, wherein the output member is at least partially disposed in the manifold.

10. The surgical barrier of claim 9, wherein the output member is a piston.

11. A method of using a surgical drape to transfer motion between a drive system of the non-sterile component and a surgical instrument, the method comprising:
   providing a surgical system including a non-sterile component having a drive system with a drive member, and further providing a surgical instrument having at least one mechanical instrument actuator moveable to cause a movement of the surgical instrument;
   providing a sterile surgical drape having a first surface, a second surface opposed to the first surface, and a fluid manifold disposed between the first and second surfaces;
   positioning the sterile surgical drape on the non-sterile component of surgical system with the first surface contacting the drive member;
   positioning the surgical instrument with the mechanical instrument actuator contacting the second surface;
   moving the drive member against the first surface to deform at least a portion of the first surface and to drive the volume of fluid through the manifold in a first fluid direction, wherein driving the fluid in the first direction deforms at least a portion of the second surface thereby moving the mechanical instrument actuator and causing movement of the instrument.

12. The method of claim 11, wherein;
   deforming at least a first portion of the first surface comprises compressing said at least a portion of the first surface; and
   deforming at least a portion of the second surface comprises expanding at least a portion of the second surface.

* * * * *